| United States Patent [19] | [11] | 4,424,398 |
| --- | --- | --- |
| McGuire et al. | [45] | Jan. 3, 1984 |

[54] PROCESS FOR PREPARATION OF ENERGETIC PLASTICIZERS

[75] Inventors: Raymond R. McGuire, Colorado Springs, Colo.; Robert E. Cochoy, Dayton, Ohio; Scott A. Shackelford, Colorado Springs, Colo.

[73] Assignee: The United States of America as represented by the Secretary of the Air Force, Washington, D.C.

[21] Appl. No.: 508,938

[22] Filed: Sep. 25, 1974

[51] Int. Cl.³ .................... C07C 79/343; C07C 76/02; C06B 25/00
[52] U.S. Cl. ................................. 568/589; 568/583; 568/588; 568/590; 149/88; 149/19.91
[58] Field of Search .......................... 149/88, 19.91; 260/614 A, 614 F, 615 A, 615 F, 612 D; 568/583, 588, 589, 590

[56] References Cited

U.S. PATENT DOCUMENTS

| 2,682,532 | 6/1954 | Adelman | 260/615 A |
| 2,872,487 | 2/1959 | Croix | 260/615 A |
| 3,129,250 | 4/1964 | Lawlor et al. | 260/615 A |
| 3,396,187 | 8/1968 | Benziger et al. | 149/88 |
| 3,808,182 | 4/1974 | Adolph | 149/88 |

FOREIGN PATENT DOCUMENTS 352474 6/1931 United Kingdom ........... 260/615 A

OTHER PUBLICATIONS

Beard et al., *J. Org. Chem.*, 38, (#21) 3673–3677 (1973).

*Primary Examiner*—Edward A. Miller
*Attorney, Agent, or Firm*—Donald J. Singer; Cedric H. Kuhn

[57] ABSTRACT

A process for synthesizing energetic ethers, esters and acetals is disclosed that comprises reacting certain alcohols with certain alkenes or alkynes in the presence of mercuric or mercurous sulfate. The products obtained are particularly useful as plasticizers, monomers or prepolymers for propellant binder systems.

10 Claims, No Drawings

PROCESS FOR PREPARATION OF ENERGETIC PLASTICIZERS

RIGHTS OF THE GOVERNMENT

The invention described herein may be manufactured and used by or for the Government of the United States for all governmental purposes without the payment of any royalty.

FIELD OF THE INVENTION

This invention relates to a process for preparing plasticizers for propellant binder compositions. In one aspect it relates to new compositions that are useful as plasticizers and/or precursors for binder compositions.

BACKGROUND OF THE INVENTION

Solid rocket propellant compositions may comprise a variety of ingredients that include, for example, an oxidant, a burning rate catalyst, a binder, and a plasticizer for the binder. Conventional plasticizers, such as phthalates, are unsatisfactory for use with propellant binders since their use results in a loss of energy when the propellant is burned. So-called energetic ethers and acetals, which have been developed as binder plasticizers, have not proven to be entirely satisfactory. Thus, the procedures followed in preparing such compounds require the reacting unsaturated bond to be conjugated with an electron-withdrawing substituent, generally a carbonyl, carboxyl or nitrile group. The presence of these substituent groups seriously degrades the energy of the products, thereby detracting from their suitability as binder plasticizers.

It is an object of this invention, therefore, to provide new energetic plasticizers for propellant binder compositions.

Another object of the invention is to provide a process for preparing the energetic plasticizers.

A further object of the invention is to provide monomeric materials and prepolymers that can be used in binder systems.

Other objects and advantages of the invention will become apparent to those skilled in the art upon consideration of the accompanying disclosure.

SUMMARY OF THE INVENTION

The present invention resides in the discovery of a process for synthesizing energetic plasticizers, monomers and prepolymers that can be used as components in propellant binder systems. Because the products do not contain energy-degrading groups, such as carbonyl, carboxyl or nitrile groups, the binder systems incorporating the products are not subject to the energy losses of prior systems. Broadly speaking, the process comprises the step of reacting, in the presence of a catalytic amount of mercuric or mercurous sulfate, 2-fluoro-2,2-dinitroethanol, 2,2-dinitro-1,3-propane diol or 2,2,2-trinitroethanol with (1) a compound having an ethynyl ether linkage, (2) a compound having an olefinic linkage which is 1,1-disubstituted or which is attached to an ether function, or (3) a compound containing a conjugated olefin linkage.

The above-described alkenes and alkynes that are reacted with alcohols in the process are selected from the group of unsaturated compounds having the following formulas:

(1) RO—C≡C—R$_1$, where R is alkyl, ethynyl or aryl, and R$_1$ is hydrogen, alkyl or aryl;

(2)

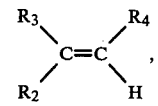

where R$_2$ is hydrogen or alkyl, R$_3$ is aryl, alkyl ether, aryl ether or vinyl ether when R$_2$ is hydrogen and R$_3$ is alkyl, aryl, alkyl ether, aryl ether or vinyl ether when R$_2$ is alkyl, and R$_4$ is hydrogen or alkyl; and (3)

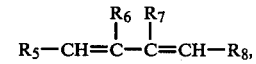

where R$_5$, R$_6$, R$_7$ and R$_8$ are hydrogen or alkyl. Examples of compounds corresponding to the foregoing formulas include methoxyacetylene, ethoxyacetylene, phenoxyacetylene, 1-methoxypropyne, divinyl ether, ethyl vinyl ether, diethynyl ether, ethyl phenylethynyl ether, 1,3-butadiene, isoprene, 2-methyl-1-pentene, 2-methoxy-1-propene, styrene, 1-methoxy-1,4-pentadiene, 2,3-dimethyl-1,3-butadiene, and the like.

In carrying out the various reactions, stoichiometric amounts of the reactants can be employed. However, it is usually preferred to use a molar excess of one of the unsaturated compounds. Thus, the mol ratio of alcohol to unsaturated compound can fall in the range of 1:1 to 1:6. The reaction is catalyzed by conducting the reaction in the presence of a catalytic amount of mercuric or mercurous sulfate. The amount of catalyst employed can vary within rather wide limits, but the weight ratio of catalyst to unsaturated compounds generally falls in the range of 1:4 to 1:20.

The reaction is carried out in a reaction medium which is a solvent for the reactants. It is usually preferred to employ as the solvent a halogenated hydrocarbon, such as methylene chloride, carbon tetrachloride, 1,2-dichloroethane, tetrachloroethane, and the like. The temperature employed in the process usually ranges from about room temperature to reflux temperature. The reaction period will vary with the reactants used, but it generally ranges from about 4 to 48 hours.

A more comprehensive understanding of the invention can be obtained by referring to the following illustrative examples which are not intended, however, to be unduly limitative of the invention.

EXAMPLE I

A run was carried out in which the reaction represented by the following equation occurred:

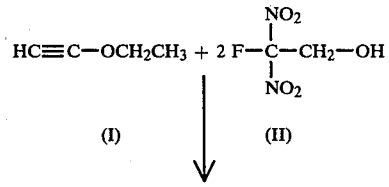

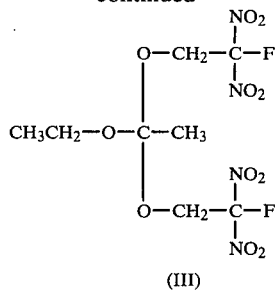

(III)

In conducting the run, a 50 ml single-necked, round bottomed flask containing a Teflon coated magnetic stirring bar was charged with 1.05 g (15 mmoles) of ethoxyacetylene (I), 25 ml of dry methylene chloride and 2.93 g (19 mmoles) of 2-fluoro-2,2-dinitroethanol (II). The reaction flask, fitted with a reflux condenser and drying tube, was cooled to ice temperature after which 0.100 g of mercuric sulfate was added. After completion of the initial exothermic reaction, the mixture was stirred at ambient temperature for 16 hours. The reaction mixture was then poured through a sintered glass filter containing a pad of about 23 g of neutral alumina (pH=7.2). The filter was washed with additional methylene chloride after which the solvent was removed from the combined filtrates in vacuo to yield 3.59 g (100% yield) of product (III) as a light yellow liquid (density 1.42 g/cc).

Analysis: Calc'd for $C_8H_{12}N_4O_{11}F_2$(III) (Wt%): C,25.42; H,3.20; N,14.82; F, 10.06. Found (Wt%): C,25.41; H,3.19; N,14.68; F,10.11.

EXAMPLE II

A run was conducted in which a solution of 1.40 g (20 mmoles) of ethoxyacetylene (I) and 2.28 g (14.8 mmoles) of 2-fluoro-2,2-dinitroethanol (II) in 40 ml of carbon tetrachloride was passed through a chromatographic column. The column ($\frac{3}{4}$" I. D.) was packed with 5 g of a mixture containing 5 weight percent of mercuric sulfate and 95 weight percent of Celite diatomaceous earth product. The effluent was concentrated, redissolved in carbon tetrachloride, and filtered through a short column of neutral alumina. After removing the carbon tetrachloride solvent, 2.27 g (81% yield) of a light yellow oil was obtained as the product (III).

EXAMPLE III

A run was carried out in which the reaction represented by the following equation occurred:

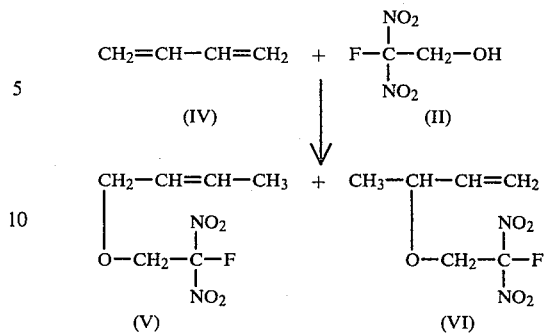

To a 250 ml glass pressure bottle there was added 5.85 g (38 mmoles) of 2-fluoro-2,2-dinitroethanol (II), 50 mls of carbon tetrachloride, and 1.5 g of mercuric sulfate. The bottle was cooled to ice temperature and 1,3-butadiene (IV) gas was bubbled into the solution until 7.8 (145 mmoles) had been dissolved. The bottle was then capped with a rubber stopper after which it was shaken for 40 hours at 55° C. The crude reaction mixture was then filtered through a short column of neutral alumina (pH=7.2) and the solvent was removed in vacuo. The crude product was then distilled to yield 1.55 g of product (V) [boiling point 40°-42° C. at 0.4 mm Hg] and 2.38 g of product (VI) [boiling point 30°-40° C. at 0.4 mm Hg]. The total yield of both isomers was 50 percent. Pure samples of products (V) and (VI) were obtained by vapor phase chromatography and were characterized by their nuclear magnetic resonance and infrared spectra and elemental analyses.

Analysis: Calc'd for $C_6H_9N_2O_5F$: C,34.62; H,4.36; N,13.46; F,9.13. Found for (V): C,34.85; H,4.39; N,13.56; F,9.05. Found for (VI): C,34.85; H,4.39; N,13.34; F,9.16.

EXAMPLE IV

A run was conducted in which the reaction represented by the following equation occurred:

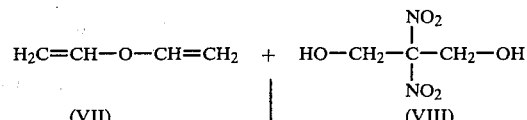

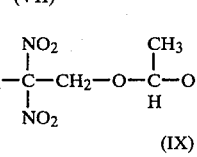

(IX)

A 50 ml single-necked, round bottomed flask containing a Teflon coated magnetic stirring bar was charged with 1.50 g (21.4 mmoles) of divinylether (VII), 20 ml of dry methylene chloride, 0.55 g (3.6 mmoles) of 2,2-dinitro-1,3-propanediol (VIII), and 0.55 g of mercurous sulfate. The reaction vessel was fitted with a condenser and drying tube, and the mixture was stirred while heating at reflux temperature for 24 hours. The solvent was then stripped in vacuo to give 0.88 g of a yellow oil. (Excess divinylether was also removed during the stripping operation). The crude product was then passed through a short column (1.5 cm ID×10 cm) of neutral alumina (pH=7.3), using methylene chloride as the eluent. Removal of the solvent in vacuo yielded 0.51 g of product (IX) (65% yield) where x equalled from 5 to 8. The polymer product was characterized by its nuclear magnetic resonance and infrared spectra.

EXAMPLE V

A series of runs was conducted in which the reaction represented by the following equations occurred:

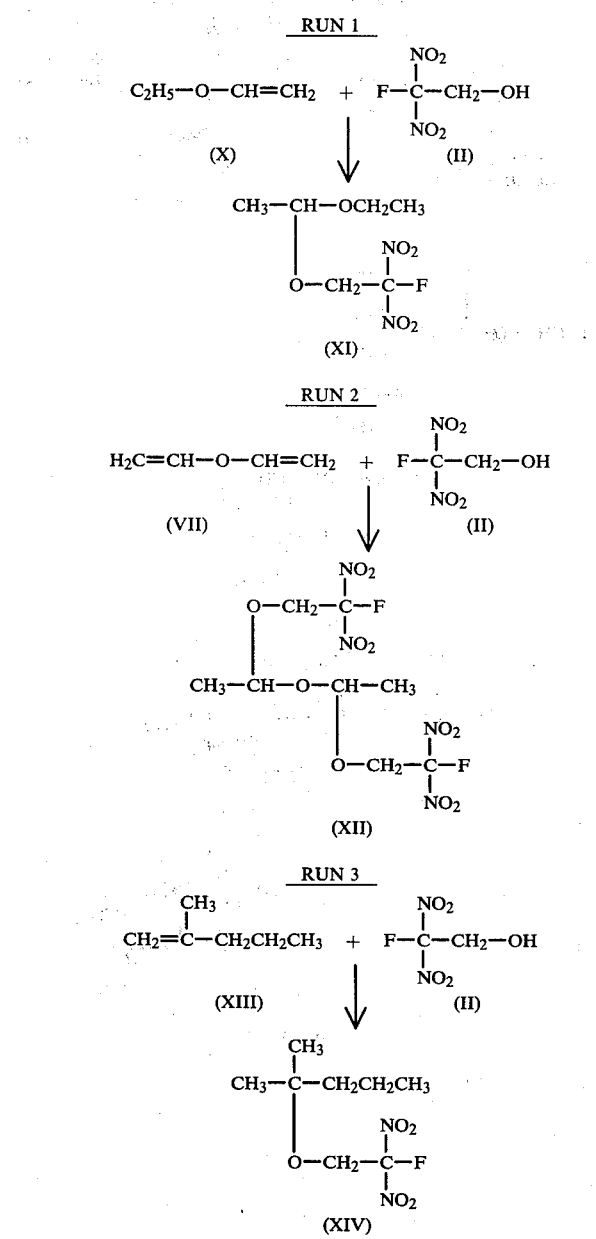

In carrying out the runs, essentially the same procedure as described in Example IV was followed. In each run, 0.200 g of mercuric sulfate catalyst and methylene chloride solvent were used. Other conditions followed and results obtained are set forth below in the table.

TABLE

| Olefin | Alcohol | Temp. | Time, hrs | Yield, % |
|---|---|---|---|---|
| Ethyl vinyl ether (X) | (II) | Ambient | 16 | 77 |
| Divinyl ether (VII) | (II) | Reflux | 16 | 100[(1)] |
| 2-Methyl-1-pentene (XIII) | (II) | Reflux | 16 | 78 |

[(1)]By varying the stoichiometry, i.e., using a 2:1 mol ratio of olefin to alcohol, a product mixture can be obtained that contains about 70 percent of the mono adduct having the following formula

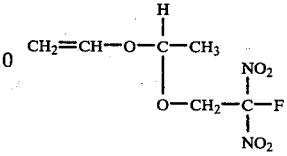

The products of Examples I, II and V are saturated compounds which are eminently suitable for use as energetic plasticizers for solid propellant binders. In this regard it is noted that the compounds do not contain energy-degrading groups as do conventional plasticizers for binder systems. The products of Example III and the product referred to in the footnote of the table of Example V are unsaturated compounds which can be used as monomers in preparing energetic binder systems. Thus, the compounds can be polymerized, e.g., with a Ziegler-type catalyst, to provide an energetic binder material. The product obtained in Example IV is a prepolymer that can be cured by a suitable curing agent, such as benzoyl peroxide, to provide an energetic binder material.

As will be evident to those skilled in the art, modification of the invention can be made in view of the foregoing disclosure without departing from the spirit and scope of the invention.

We claim:

1. A process for synthesizing energetic plasticizers and precursors for binder systems which comprises reacting, in the presence of a catalytic amount of mercuric or mercurous sulfate, an alcohol selected from the group consisting of 2-fluoro-2,2-dinitroethanol, 2,2-dinitro-1,3-propane diol and 2,2,2-trinitroethanol with an unsaturated compound selected from the group of compounds having the following formulas:

(1) RO—C≡C—$R_1$, where R is alkyl, ethynyl or aryl and $R_1$ is hydrogen, alkyl or aryl;

(2)

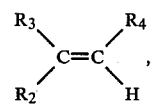

where $R_2$ is hydrogen or alkyl, $R_3$ is alkyl ether, aryl ether or vinyl ether when $R_2$ is hydrogen, and $R_3$ is alkyl, aryl, alkyl ether, aryl ether or vinyl ether when $R_2$ is alkyl and $R_4$ is hydrogen or alkyl; and (3)

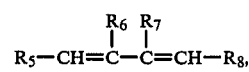

where $R_5$, $R_6$, $R_7$ and $R_8$ are hydrogen or alkyl, the mole ratio of alcohol to unsaturated compound ranging from 1:1 to 1:6 and the reaction being conducted in a solvent which is inert to the alcohol and unsaturated compound at a temperature ranging from about room temperature to reflux temperature for a period ranging from about 4 to 48 hours.

2. The process according to claim 1 in which the solvent is a halogenated hydrocarbon.

3. The process according to claim 2 in which the solvent is methylene chloride, carbon tetrachloride, 1,2-dichloroethane, or tetrachloroethane.

4. The process according to claim 1 in which 2-fluoro-2,2-dinitroethanol and ethoxyacetylene are reacted.

5. The process according to claim 1 in which 2-fluoro-2,2-dinitroethanol and 1,3-butadiene are reacted.

6. The process according to claim 1 in which 2,2-dinitro-1,3-propanediol and divinyl ether are reacted.

7. The process according to claim 1 in which 2-fluoro-2,2-dinitroethanol and ethyl vinyl ether are reacted.

8. The process according to claim 1 in which 2-fluoro-2,2-dinitroethanol and 2-methyl-1-pentene are reacted.

9. A process for synthesizing energetic plasticizers and precursors for binder systems which comprises reacting, in the presence of a catalytic amount of mercuric or mercurous sulfate, 2-fluoro-2,2-dinitroethanol with an unsaturated compound selected from the group of compounds having the following formulas:

(1) $RO-C\equiv C-R_1$, where R is alkyl, ethynyl or aryl and $R_1$ is hydrogen, alkyl or aryl;

(2)

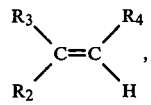

where $R_2$ is hydrogen or alkyl, $R_3$ is alkyl ether, aryl ether or vinyl ether when $R_2$ is hydrogen, and $R_3$ is alkyl, aryl, alkyl ether, aryl ether or vinyl ether when $R_2$ is alkyl and $R_4$ is hydrogen or alkyl; and (3)

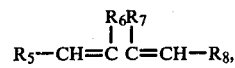

where $R_5$, $R_6$, $R_7$ and $R_8$ are hydrogen or alkyl, the mole ratio of 2-fluoro-2,2-dinitroethanol to unsaturated compound ranging from 1:1 to 1:6 and the reaction being conducted in a solvent which is inert to the alcohol and unsaturated compound at a temperature ranging from about room temperature to reflux temperature for a period ranging from about 4 to 48 hours.

10. As a new composition of matter, a compound selected from the group of compounds having the following formulas:

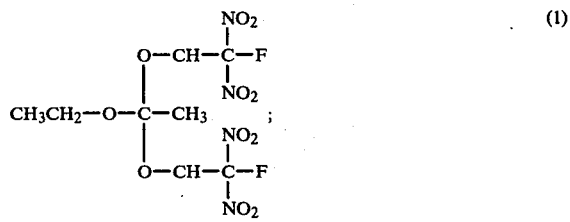

(1)

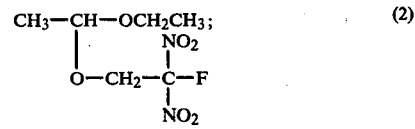

(2)

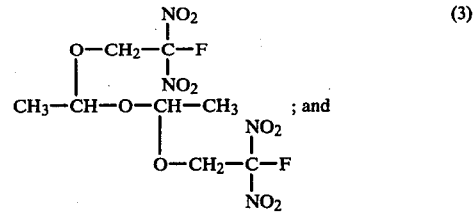

(3) ; and

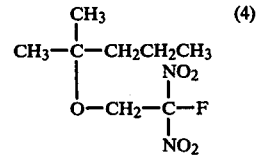

(4)

* * * * *